United States Patent
Kessler

(12) 
(10) Patent No.: US 6,176,988 B1
(45) Date of Patent: Jan. 23, 2001

(54) MEMBRANE ELECTRODE FOR MEASURING THE GLUCOSE CONCENTRATION IN FLUIDS

(76) Inventor: Manfred Kessler, Schlehenstrasse 14, DE-91056 Erlangen (DE)

(*) Notice: Under 35 U.S.C. 154(b), the term of this patent shall be extended for 0 days.

(21) Appl. No.: 09/194,453
(22) PCT Filed: May 26, 1997
(86) PCT No.: PCT/DE97/01114
§ 371 Date: Nov. 23, 1998
§ 102(e) Date: Nov. 23, 1998
(87) PCT Pub. No.: WO97/45719
PCT Pub. Date: Dec. 4, 1997

(30) Foreign Application Priority Data

May 25, 1996 (DE) .................................. 196 21 241

(51) Int. Cl.⁷ .................... G01N 27/26; G01N 27/327
(52) U.S. Cl. .................... 204/403; 204/418; 204/415
(58) Field of Search .................... 204/403, 409, 204/415, 416, 418, 419

(56) References Cited

U.S. PATENT DOCUMENTS

| | | |
|---|---|---|
| 4,579,642 | 4/1986 | Niiyama et al. ............ 204/403 |
| 5,387,328 | 2/1995 | Sohn .................... 204/403 |

FOREIGN PATENT DOCUMENTS 6 2274 254   11/1997   (JP) .

OTHER PUBLICATIONS

Silber et al., "Thick–Film Multichannel Biosensors For Simultaneous Amperometric And Potentiometric Measurements," *Sensors and Actuators B30* (1996) pp. 127–132.

*Primary Examiner*—T. Tung
*Assistant Examiner*—Alex Noguerola
(74) *Attorney, Agent, or Firm*—Hoffman & Baron, LLP

(57) ABSTRACT

The present invention concerns a membrane electrode for measuring glucose concentration in liquids, comprising: a base membrane with at least one noble metal electrode which is arranged on one side of the base membrane; a proton-selective ion membrane arranged on the base membrane and the noble metal electrode; and a double membrane which is arranged on the ion membrane and in which glucose oxidase is contained in a suitable medium, and also an electronic circuit for operation of the membrane electrode comprising: a stabilised polarisation voltage source; two high-impedance amplifiers; a parallel resistor; an element for processing and storage of the measured parameter; and an output means.

31 Claims, 13 Drawing Sheets

US 6,176,988 B1

MEMBRANE ELECTRODE FOR MEASURING THE GLUCOSE CONCENTRATION IN FLUIDS

FIELD OF THE INVENTION

The present invention concerns a membrane electrode for measuring the glucose concentration in liquids, and an electronic circuit for operation of the membrane electrode.

BACKGROUND OF THE INVENTION

EP-A 0 141 178 discloses an arrangement for measuring the level of concentration of a substance, with which it is possible to determine levels of concentration of $H_2O_2$. The arrangement has a measuring electrode comprising noble metal which is separated from an electrolyte by a lipophilic membrane. In that case the membrane contains lipophilic ions, in particular anions, and/or carrier-bonded ions and is proton-impermeable. In a particular embodiment, contained in the electrolyte space or chamber which is separated from the electrode by the lipophilic membrane is an enzyme which converts a diffusible substance inter alia into $H_2O_2$, the concentration of which is measured by the arrangement and thus makes it possible to determine the concentration of the substance.

That arrangement for measuring the concentration of a substance suffers from the disadvantage that the measured parameter varies relatively substantially during the measurement procedure, that is to say it is subject to a certain amount of drift.

SUMMARY OF THE INVENTION

An object of the present invention is to provide a membrane electrode for measuring the glucose concentration in a liquid, which avoids the problem encountered in the above-discussed arrangement and which can be economically produced.

A further object of the invention is to provide a membrane electrode for measuring glucose concentration in a liquid, which is of a simple structure while affording reliability in operation and operating results of enhanced accuracy.

A further object of the invention is to provide an electronic circuit for the operation of a membrane electrode for measuring the glucose concentration in a liquid, which contributes to allowing the electrode to operate in optimised fashion.

The foregoing and other objects are attained by a membrane electrode for measuring the glucose concentration in liquids, comprising: a base or main membrane with at least one noble metal electrode which is arranged on a first side of the base or main membrane; a proton-selective ion membrane which is arranged on the base or main membrane and the noble metal electrode; and a double membrane which is arranged on the ion membrane and in which glucose oxidase is contained in a suitable medium.

The foregoing and other objects of the present invention are further attained by an electronic circuit for operation of the membrane electrode comprising: a stabilised polarisation or biasing voltage source; first and second high-impedance amplifiers; a parallel resistor; an element for processing and storage of the measured parameter; and an output means.

It will be noted at this point that conventional electrodes with large noble metal surfaces exhibit a high level of sensitivity in relation to convection. That means that changes in the capillary flow which cause changes in convection within the diffusion zone of the electrode induce large changes in the electrode signal. In consideration of that fact, microelectrodes with an electrode diameter of below 50 μm with a low level of convection sensitivity are employed. Microelectrodes of that kind however suffer from the disadvantage that they have a relatively high degree of drift. It is generally in the range of between 2 and 3% per hour. The use of microelectrodes for measurement operations with an adequate degree of accuracy is therefore only possible if that drift is suitably corrected. That requires frequent calibration operations with at least two solutions or standard gases.

In contrast the electrodes according to the invention provide that the noble metal surface is covered with a protective lipophilic membrane which permits only hydrophobic and gaseous species to reach the electrode. In accordance with the invention moreover a double membrane is arranged on the ion membrane, with glucose oxidased in a suitable medium being contained in the double membrane.

The principle of potentiometric-polarographic $H_2O_2$-measurements is a combination of two different electrochemical processes, amperometry and potentiometry. The combination of those two measuring processes in one electrode is based on the observation that electrodes in which the ion membrane was brought into contact for example with platinum react on hydrogen. Investigation of that unexpected phenomenon showed that hydrogen at the platinum surface is oxidised in accordance with the following electrochemical reaction:

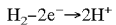

The protons formed are transported by means of ion carrier molecules through the ion membrane. The flux of protons through the ion membrane, which is produced by the ion carrier molecules, produces a membrane potential which can be potentiometrically determined. Precise analysis of the results showed that a lipophilic PVC-membrane with a proton-carrier contained therein acquires multifunctional properties if it is brought into contact with a noble metal surface instead of an internal electrolyte solution, for example 3- or 4-molar KCl.

It is to be noted that a crucial precondition for activation of a potentiometric-polarographic noble metal electrode of that kind is adequate hydration thereof. That is achieved by the diffusion of water vapor through the lipophilic ion membrane. The water molecules reaching the metal surface there form a dipolar layer. Subsequently a Helmholtz polarisation layer is developed with OH-anions as a charged layer if the electrode is used as an anode. Because of the absence of ions other than OH⁻ and H⁺ that Helmholtz layer exclusively contains water and dissociation products of water, that is to say $OH^-$-ions and $H^+$-ions.

The fact that an intermediate layer of between about 250 and 300 nm is formed between the noble metal surface and the ion membrane by the hydration step results in useful electrochemical interactions which do not exist in conventional electrode systems.

If $H_2O_2$ diffuses through the ion membrane, it is oxidised at the polarised noble metal surface and the protons originating from that redox reaction accumulate by virtue of the diffusion resistance of the ion membrane in the intermediate space produced by hydration between the electrode surface and the ion membrane. On the other hand there is a proton flux through the membrane, that flux depending on the thickness of the membrane, the concentration and mobility of the $H^+$-carriers in the lipophilic membrane, the activity of the protons in the intermediate space between the noble metal electrode and the ion membrane and the electrical field strength between the noble metal surface and the outer enzyme space. Those parameters can be suitably adjusted in accordance with the requirements involved by virtue of the configuration of the electrode according to the invention in terms of the thickness of the membrane, the applied electrical field and the other specified parameters, so that the flux of protons through the ion membrane results in the formation of two proton gradients and corresponding potential gradients. The first gradient is developed in the water-filled intermediate space between the noble metal electrode and the ion membrane while the second occurs within the membrane.

Polarographic electrodes can be used as reducing or oxidising electrochemical systems. They comprise a polarisable metal electrode, a non-polarisable reference electrode (for example Ag/AgCl) and a polarisation voltage source. The specific signal is the current which is produced by the redox reaction of the chemical species to be analysed. In principle all molecules which reach the metal surface by diffusion are completely oxidised or reduced.

Accordingly the concentration of the species to be analysed falls from its original or initial concentration value in the sample to zero at the surface of the polarised electrode. The number of molecules which diffuse to the surface depends on their flux which is proportional to their concentration but independent of their activity. The relationship between the concentration of the species and the measured redox current is therefore linear.

The activity of ions is measured by potentiometric electrodes. The activity of chemical species is defined as the degree of free mobility of ions or molecules. The theoretical basis for activity measurements in respect of cations or anions is given by the Nernst equation which states that the activity of ions decreases with the logarithm of the increasing ion concentration. The principle of ion measurements by glass electrodes or modern ion electrodes is that ions are reversibly incorporated in accordance with the level of ion activity in a hydrated glass membrane or a suitable ion carrier. In the case of ion electrodes the mechanism of incorporation of ions is similar to charging and discharging of capacitors. According to Moody and Thomas, Selective Ion sensitive Electrodes, Marrow Watford, England 1971, the membrane used in ion-conduction electrodes can be referred to as a liquid membrane.

In comparison with the polarisation voltage of conventional $H_2O_2$-, $H_2$- and $pO_2$-electrodes which is in the range of 700 mV a voltage of between 200 and 300 mV has advantageously proven to be sufficient for the membrane electrode according to the invention. In order to achieve relatively stable redox currents, conventional electrodes require polarisation times of from one to ten hours, in which case there is still a drift of 3% per hour. In contrast thereto the electrodes according to the invention have polarisation times in the range of seconds, in which respect it is particularly advantageous that the drift is substantially less in spite of the very short polarisation time. One reason for this could be the very specific properties of the Helmholtz layer which exclusively consists of $OH^-$ and $H^+$-ions. Electrochemical secondary reactions are also advantageously excluded because the noble metal surface is closed by a lipophilic membrane and is therefore of very high purity. Accordingly there cannot be any poisoning of the electrode surface by virtue of the deposit of metals, metal compounds and salts with low levels of solubility coefficients and the like.

The arrangement of the various membranes in in the electrode structure in accordance with the invention is particularly advantageous as in particular the additional arrangement of a double membrane in which glucose oxidase is contained in a suitable medium on the ion membrane means that it is possible to reduce the consumption of reducible ($O_2$) or oxidisable species ($H_2O_2$, $H_2$) to such a low level that the electrodes according to the invention do not have any convention sensitivity, even if large noble metal anodes or cathodes are used. In addition potentiometric determination of very small $H_2O_2$-oxidation flows is made possible, thereby affording the option of measuring levels of glucose concentration with extreme long-term stability with an infinitely low level of glucose consumption.

In a particular embodiment of the present invention the base membrane is arranged on an insulating membrane or a carrier foil or sheet. In that respect it is particularly advantageous if the insulating membrane or carrier foil is such that it encloses the entire electrode structure laterally and below so that the electrode can come into contact with the environment only with one surface. That affords a high degree of certainty and reliability in terms of avoiding leakage flows and substance exchange can take place only by way of the defined surface of the double membrane, which is directed towards the glucose-bearing solution.

So that such leakage phenomena are particularly effectively avoided, the successive membrane layers of the electrode structure can be welded together.

In a further embodiment of the membrane electrode according to the invention the carrier foil or insulating membrane, the base membrane with the electrode and the proton-selective ion membrane are enclosed by an outer membrane, wherein the double membrane in which glucose oxidase is contained in a suitable medium is arranged on the outer membrane over the ion membrane. In that respect it is particularly advantageous if the intermediate space between the carrier foil or insulating membrane, the base membrane with the electrode, the proton-selective ion membrane and the outer membrane is filled with an electrolyte gel.

It is preferred for the electrode to be extended from the electrode structure with a cable connecting it to a suitable electronic measuring arrangement, in a tube or hose. The tube or hose is preferably welded or glued to the outer membrane.

In a structure of that kind, it is preferable if the intermediate space between the cable and the hose is also filled with an electrolyte gel. In that case the electrolyte gel serves for contacting of the reference electrode or the reference electrode system, which advantageously prevents possible contamination of the liquids to be analysed by a reference electrode.

Noble metal electrodes are preferably used in the electrodes according to the invention, with gold and platinum being particularly preferred as the material involved.

The ion membrane generally contains a liquid phase, wherein ligand molecules are contained in particular in the liquid phase of the ion membrane, the ligand molecules being mobile within the membrane.

The ligand molecules are preferably tridodecylamine.

As electrochemical reactions are usually temperature-dependent, it is preferable for a thermal sensor to be arranged in the overall structure according to the invention of the electrode. In that way, correction of temperature-conditioned variations in measurement values is possible by virtue of continuing temperature monitoring during the measurement procedure. Generally available thermocouple elements which are used in terms of temperature measurement on or in a living body can be used in that case as the thermal sensor.

The electrode structure according to the invention can also advantageously be miniaturised, in which case thin film technologies can preferably be used in the production of miniaturised electrodes of that kind, which makes it possible to provide inexpensive electrodes which can be used as disposable electrodes. It is also possible for a plurality of measurement locations, for example two, three or four measurement locations, to be provided in a miniaturised electrode structure. That desirably makes it possible to provide for the simultaneous measurement at a corresponding number of measurement points for example on the cheek mucous membrane or the gingiva. When the individual measurement values are compared, the level of certainty of determination is increased, it is then possible to determine local differences.

For corresponding uses it is preferred for the electrode structure according to the invention to be arranged on a holding means. A holding means of that kind for example can preferably be of such a design configuration that it is adapted to be fitted on to one or more teeth or it can be in the form of a clip. That makes it possible to measure the level of glucose concentration in the mucous membrane.

In a preferred feature the electrode structure is arranged on or in a pad, for example of silicone rubber, so that it then becomes possible to measure levels of glucose concentration on surfaces of organs, for example during operations.

In a further preferred embodiment of the membrane electrode the base membrane is formed by a plastic fiber, while the electrode, the proton-selective ion membrane and the double membrane containing glucose oxidase enclose the plastic fiber. An electrode of such a configuration can be used as an insertion or puncture electrode or a cathode electrode in micro- or minimal-invasive interventions.

The membrane electrode according to the invention however also makes it possible to determine glucose in blood and liquid samples in an automatic analysis apparatus. For that purpose the electrode structure according to the invention is provided in a capillary or is so coupled to a capillary that the surface of the glucose oxidase-containing double membrane is connected to the internal space of the capillary. The electrode structure according to the invention can thus also be used in automatic analysis operations which are employed in clinics and/or generally laboratories in which liquids are investigated in regard to the glucose content. That can also be the case for example in investigating foodstuffs.

In the hitherto preferred embodiments of the membrane according to the invention, it is advantageous, for various purposes, to arrange a reference electrode with the membrane electrode together in a component or on a holding means.

The electronic circuit for operation of the membrane electrode with a stabilised polarisation voltage source, first and second high-impedance amplifiers, a parallel resistor, an element for processing and storage of the measured parameter and an output means is preferably of such a design configuration that it is divided into two units which are spatially separated from each other.

In an advantageous embodiment the units are connected together by way of a cable. In another advantageous embodiment of the electronic circuit according to the invention the units are connected by electro-optical means or are in communication with each other by electro-optical means.

The parallel resistor of the electronic circuit generally involves a resistance of between about $10^7$ and $10^{11}\Omega$, particularly preferably a resistance of $10^9\Omega$. The parallel resistor determines the order of magnitude of oxidation of $H_2O_2$ and consequently the oxidation currents generated in the circuit. As high oxidation rates make the glucose sensor sensitive to convection and the glucose oxidase would have to have high conversion rates in order to produce large amounts of $H_2O_2$, it is advantageous to avoid excessively high currents. With a resistance of between about $10^{10}$ and $10^{11}\Omega$ therefore glucose measurement procedures are still possible, but only with a limited level of accuracy, which however can certainly be sufficient for certain uses. With a resistance of below $10^9\Omega$, that is to say in a range of between about $10^7$ and $10^8\Omega$, the gradient and the shape of the calibration curves changes, which also has a disadvantageous effect on the degree of measuring accuracy.

It is therefore particularly preferred if the parallel resistor is of a resistance of $10^9\Omega$, as the best measurement results are then achieved with the overall arrangement.

Further objects, features and advantages of the invention will be apparent from the following description of preferred embodiments.

DESCRIPTION OF PREFERRED EMBODIMENTS

Figure 1:
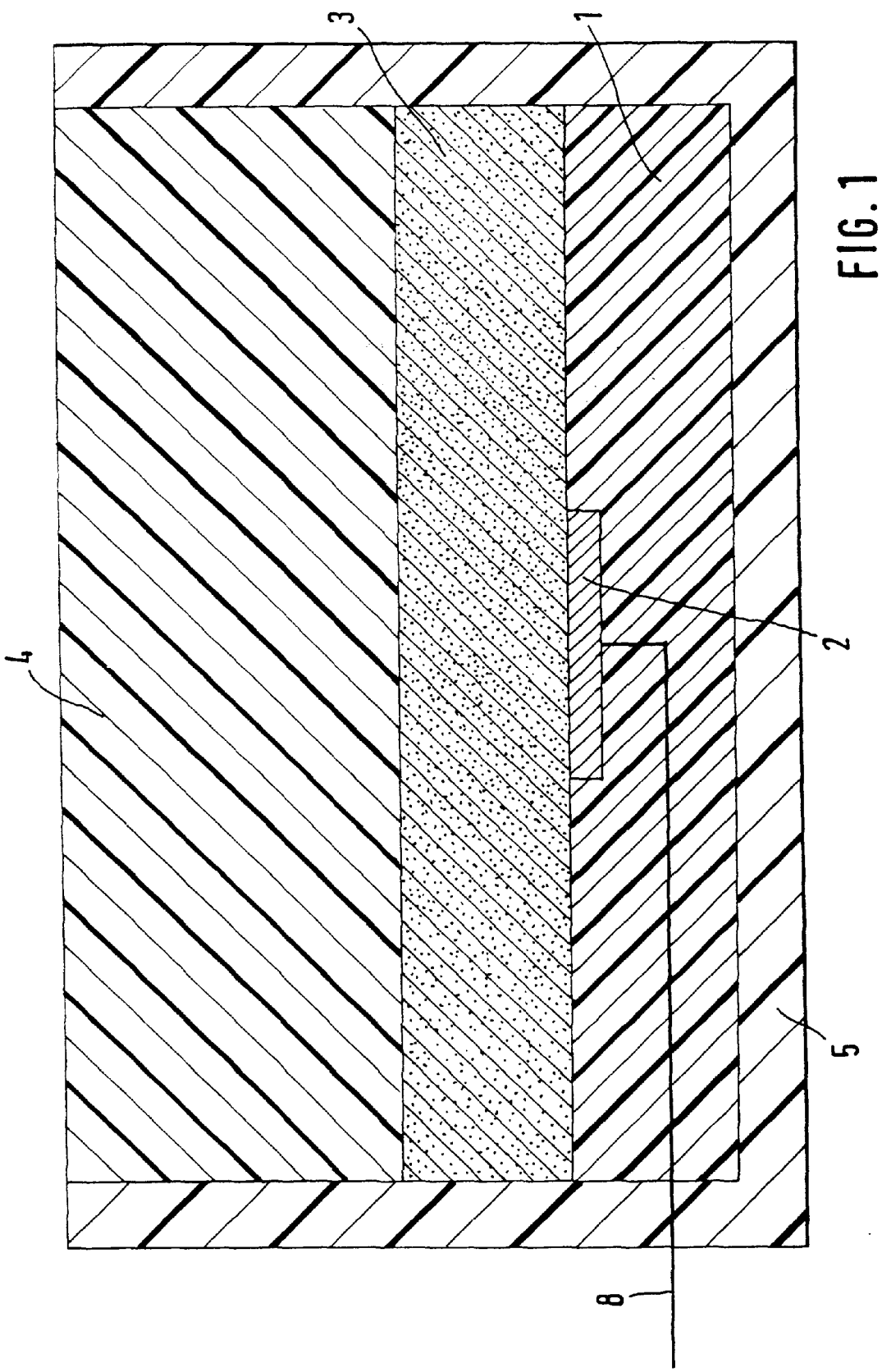
FIG. 1 is a diagrammatic representation of a membrane electrode according to the invention.

Referring to FIG. 1, shown therein in diagrammatic form is an embodiment of a membrane electrode according to the invention for measuring the glucose concentration in liquids. It comprises a base or main membrane 1 with a noble metal electrode 2 which is arranged on one side of the base membrane 1, a proton-selective ion membrane 3 which is arranged on the base membrane 1 and the noble metal electrode 2, and a double membrane 4 which is arranged on the ion membrane 3 and in which 31 is contained in a suitable medium. In the embodiment illustrated in FIG. 1 the base membrane 1 is arranged on an insulating membrane or a carrier foil or sheet 5, wherein the insulating membrane or the carrier foil or sheet 5 encloses the electrode structure laterally and at the bottom.

Figure 2:
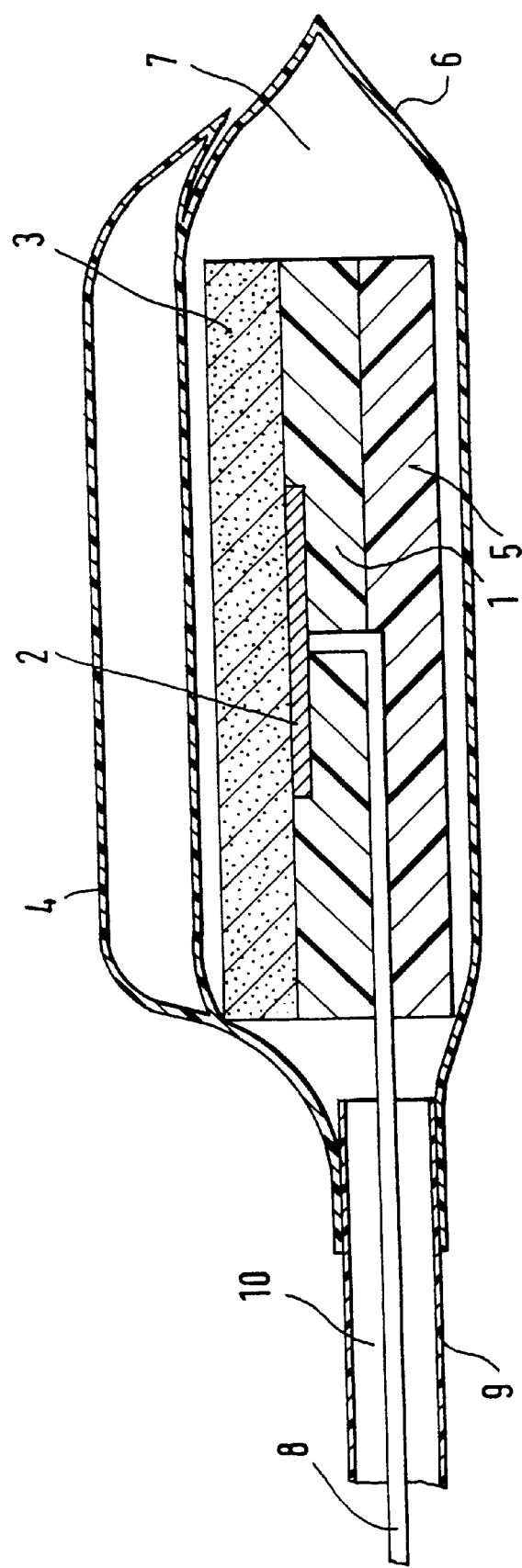
FIG. 2 is a diagrammatic representation of the membrane electrode according to the invention in another embodiment.

FIG. 2 shows an embodiment of the membrane electrode according to the invention in which the carrier foil or insulating membrane 5, the base membrane 1 with the electrode 2 and the proton-selective ion membrane 3 are enclosed by an outer membrane 6 and the double membrane 4 in which glucose oxidase 31 is contained in a suitable medium is arranged on the outer membrane 6.

In the embodiments shown in FIG. 1 and FIG. 2 the various membranes which are arranged one over the other are advantageously welded together as that avoids leakage currents. In the embodiment shown in FIG. 2 it is also advantageous if an intermediate space 7 between the carrier foil or insulating membrane 5, the base membrane 1 with the electrode 2, the proton-selective ion membrane 3 and the outer membrane 6 is filled with an electrolyte gel, in which case the electrolyte gel serves for contacting the reference electrode or the reference electrode system respectively. That affords the advantage of avoiding possible contamination of the liquid to be analysed, by a reference electrode.

The electrode 2 is connected by a cable 8 to an electronic measuring circuit arrangement. The cable 8 is extended from the electrode structure in a tube or hose 9. The hose 9 is connected to the outer membrane 6, being preferably glued and particularly preferably welded thereto. The intermediate space 10 between the cable 8 and the hose 9 is also filled with electrolyte gel. Gold or platinum is preferably used for the noble metal electrode, while thin-film technologies are preferably employed to produce the electrodes according to the invention, permitting inexpensive production of the electrodes according to the invention in large numbers. In particular CVD- or PVD-processes can be used here.

The base membrane 1 is preferably produced from an impermeable PVC while the ion membrane 3 is preferably produced from a PVC-material which as a liquid phase contains a plasticiser and contained in turn in that plasticiser are ligand molecules which can complex $H^+$-ions, Basically all molecules which are soluble in the respective plasticiser used or which are miscible therewith and which can complex $H^+$-ions fall to be considered as ligand molecules, with tridodecylamine being particularly preferred. The thickness of the membranes used is respectively of an order of magnitude of 100–300 $\mu$m and the specific total activity of the glucose oxidase 31 in the double membrane 4 is preferably approximately 1 mMol/min.

Figure 3:
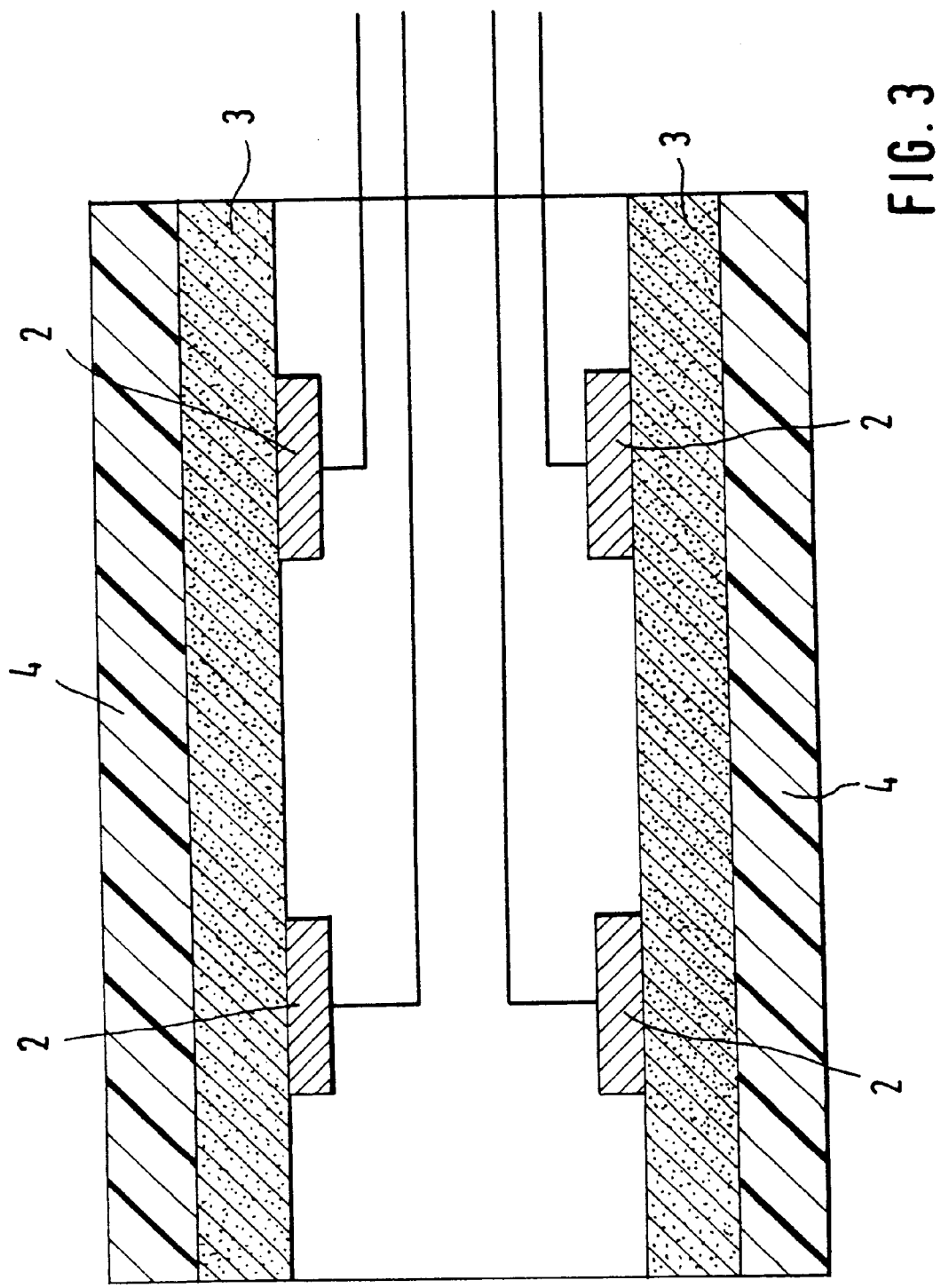
FIG. 3 shows an embodiment of the membrane electrode according to the invention with four measuring locations.

In the embodiment illustrated in FIG. 3 the electrode structure has four measuring locations, that is to say four noble metal electrodes 2 are arranged in the electrode structure, wherein the noble metal electrodes 2 are each respectively covered with a proton-selective ion membrane 3 and a double membrane 4 which contains glucose oxidase 31 in a suitable medium.

Figure 4:
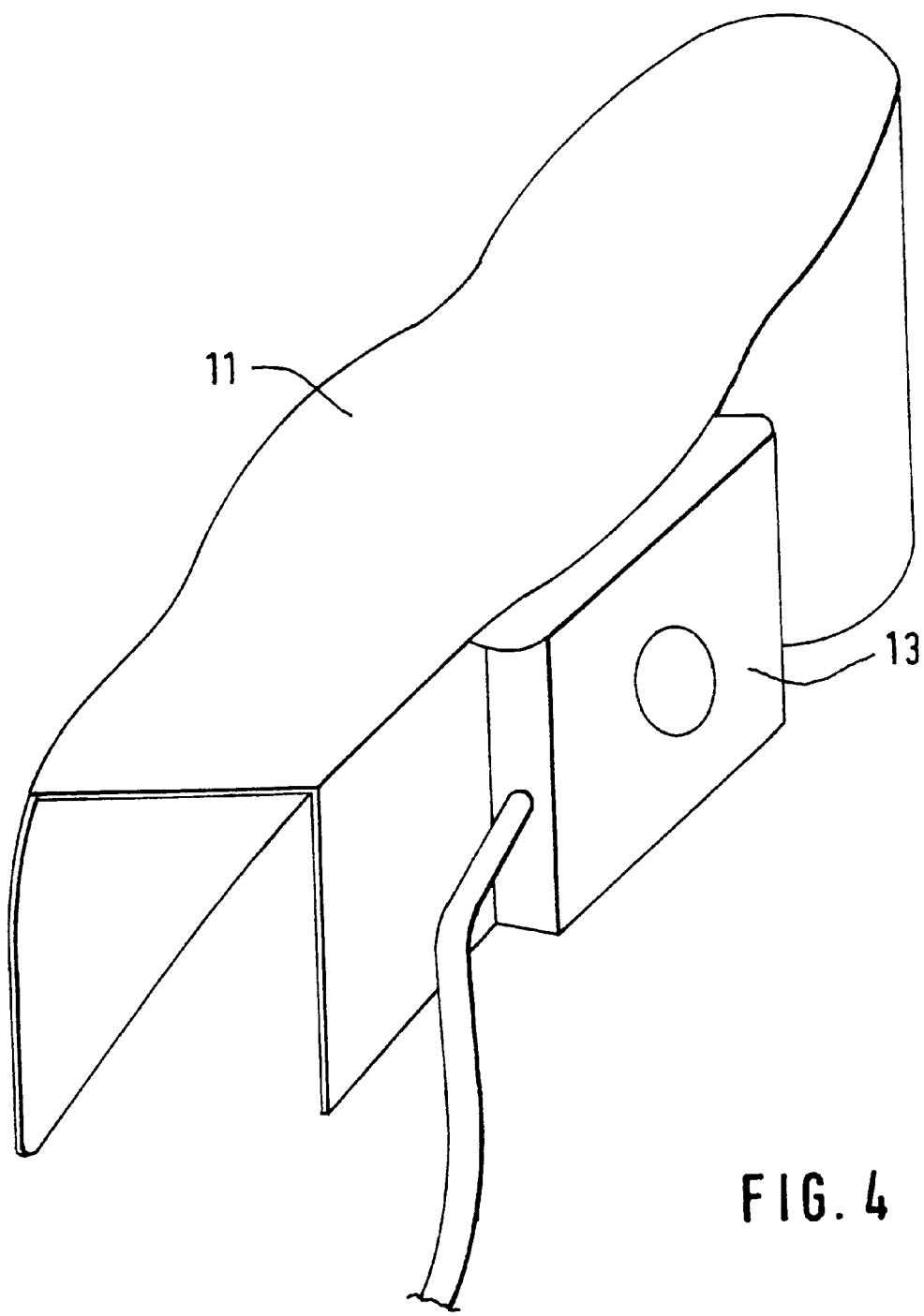
FIG. 4 shows an embodiment of the membrane according to the invention, in which it is arranged on a holding means which can be fitted on to three teeth.
Figure 5:
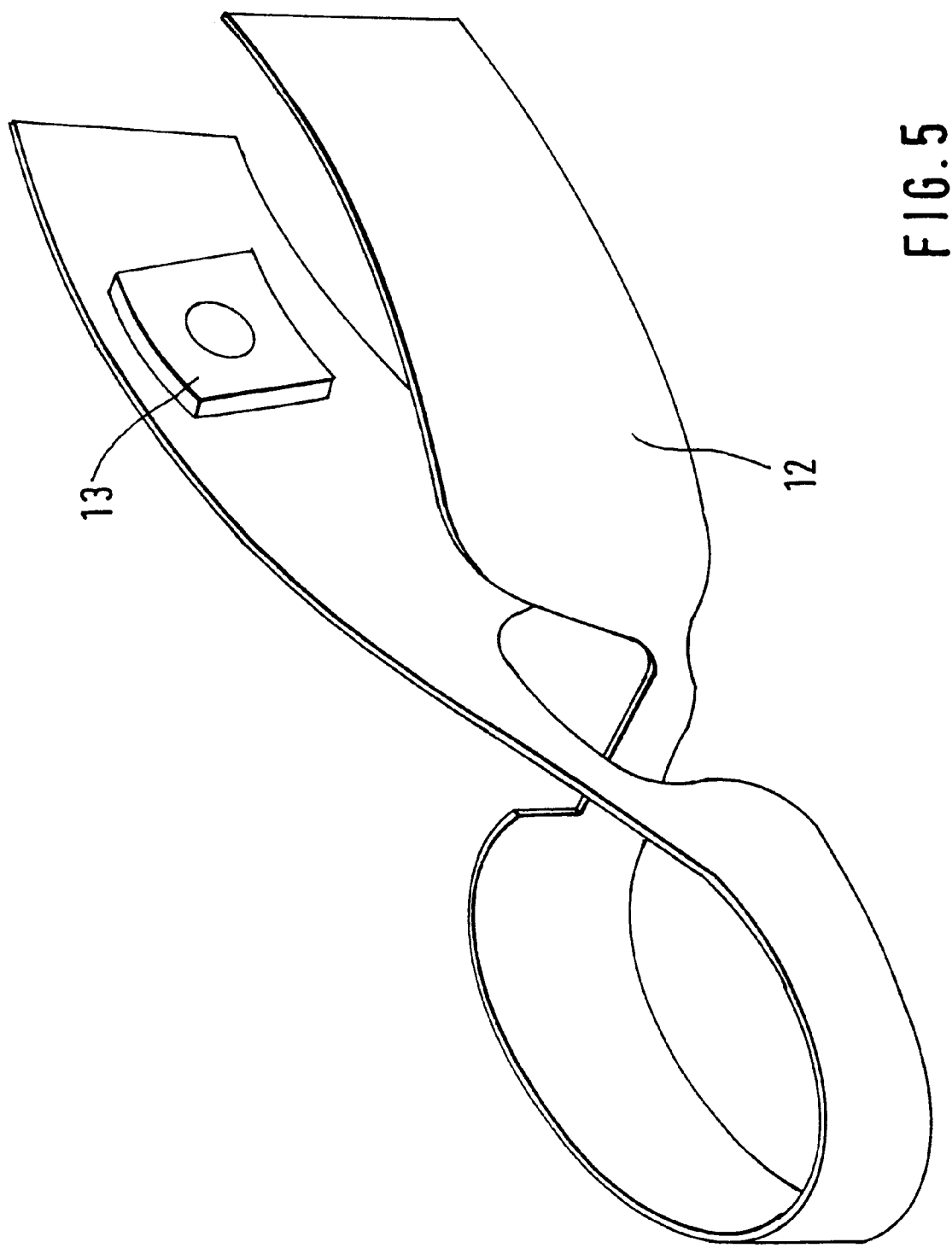
FIG. 5 shows an embodiment of the membrane electrode according to the invention in which it is arranged on a clip or clamp.

Referring to FIGS. 4 and 5, shown therein are respective holding means 11, 12 on which the membrane electrode, here generally identified by reference numeral 13, is mounted. The holding means 11 shown in FIG. 4 serves for fixing on three teeth, and it can be fitted on to three teeth, while in FIG. 5 the holding means is formed by a clip or clamp 12.

Figure 6:
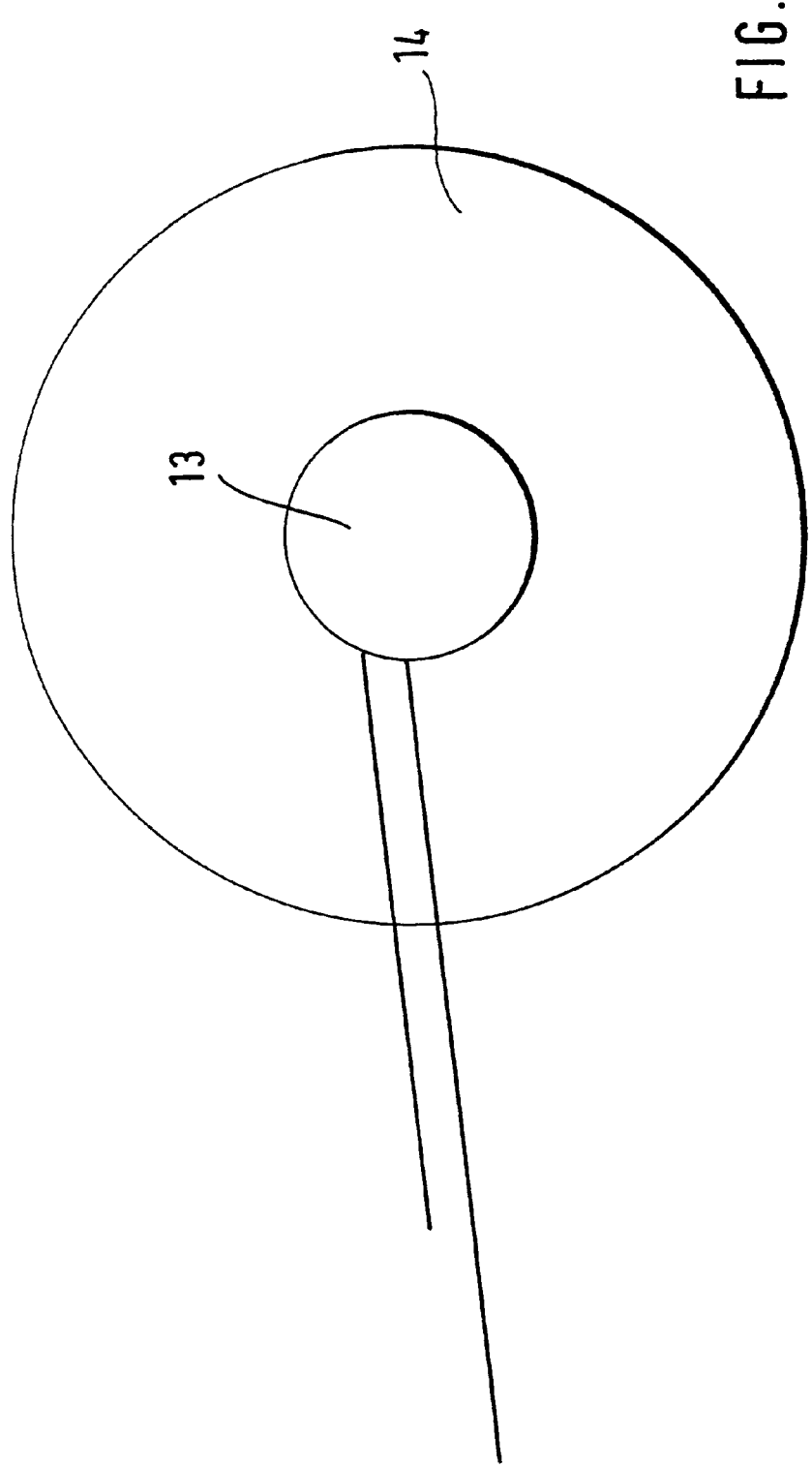
FIG. 6 shows an embodiment of the membrane electrode according to the invention in which it is arranged in a pad, preferably of silicone rubber.

The embodiment illustrated in FIG. 6 comprises a membrane electrode 13 which is arranged in a pad 14 of silicone rubber, as is preferably used for measuring levels of glucose concentration on surfaces of organs, as the distribution of weight to the pad 14 prevents the function of the organ being adversely affected by an excessively high pressure applied to the organ.

Figure 7:
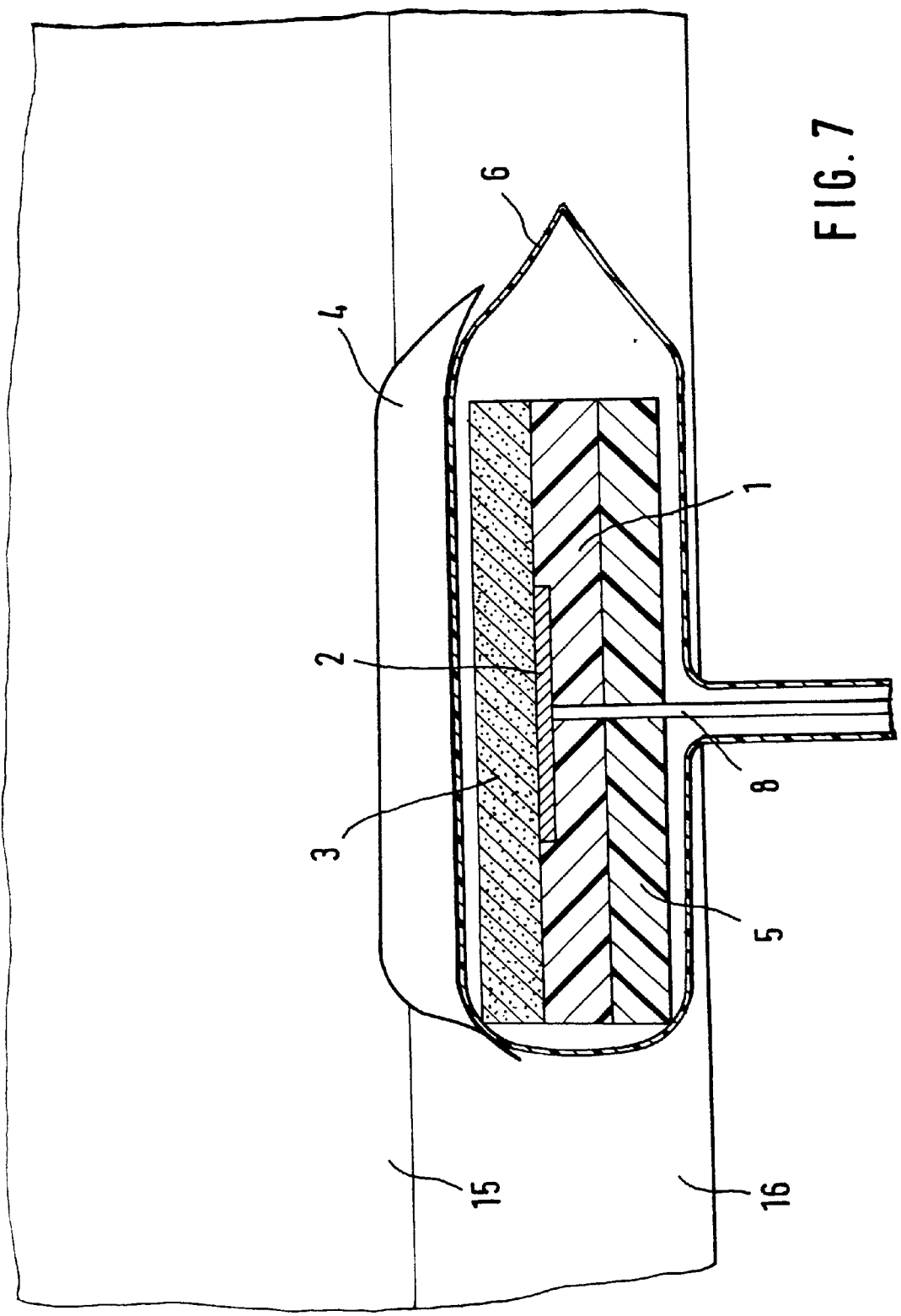
FIGS. 7 and 8 show an embodiment of the membrane electrode according to the invention in which it is arranged in or coupled to a capillary.
Figure 8:
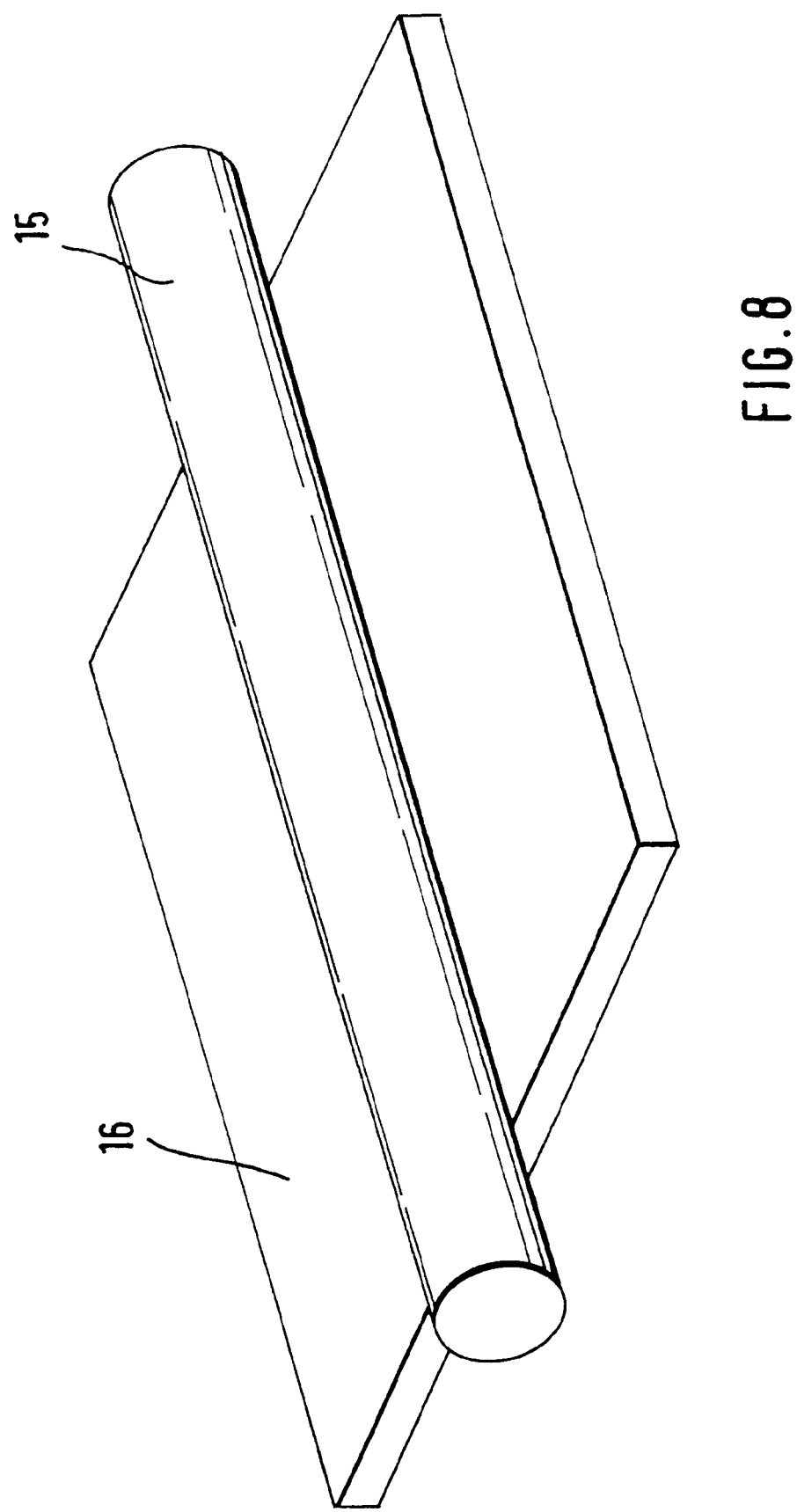

In the case of the embodiment shown in FIGS. 7 and 8, the electrode arrangement is coupled to a capillary diagrammatically indicated at 15. In this case, the capillary 15 is preferably arranged on a base plate 16 in which the electrode structure with double membrane 4, outer membrane 6, ion membrane 3, noble metal electrode 2 with cable 8, base membrane 1 and insulating membrane 5 is in turn integrated.

Figure 9:
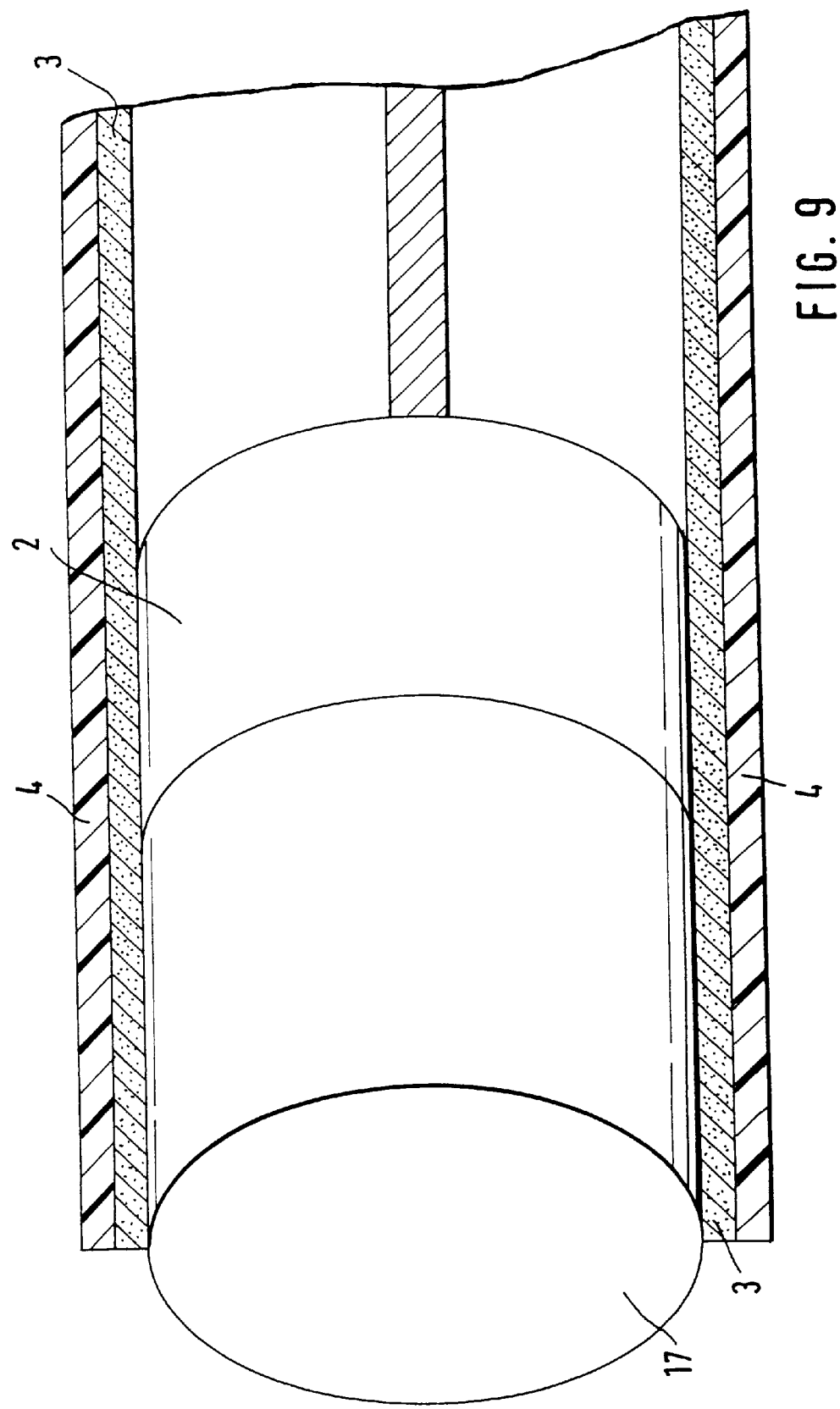
FIG. 9 shows an embodiment of the membrane electrode according to the invention in which it is in the form of an insertion and/or catheter electrode.

In the embodiment shown in FIG. 9, an insertion or catheter electrode is embodied with the structure in accordance with the present invention. In this case the base membrane is formed by a plastic fiber 17, wherein the electrode 2, the proton-selective ion membrane 3 and the glucose oxidase-containing double membrane 4 enclose the plastic fiber 17.

Figure 10:
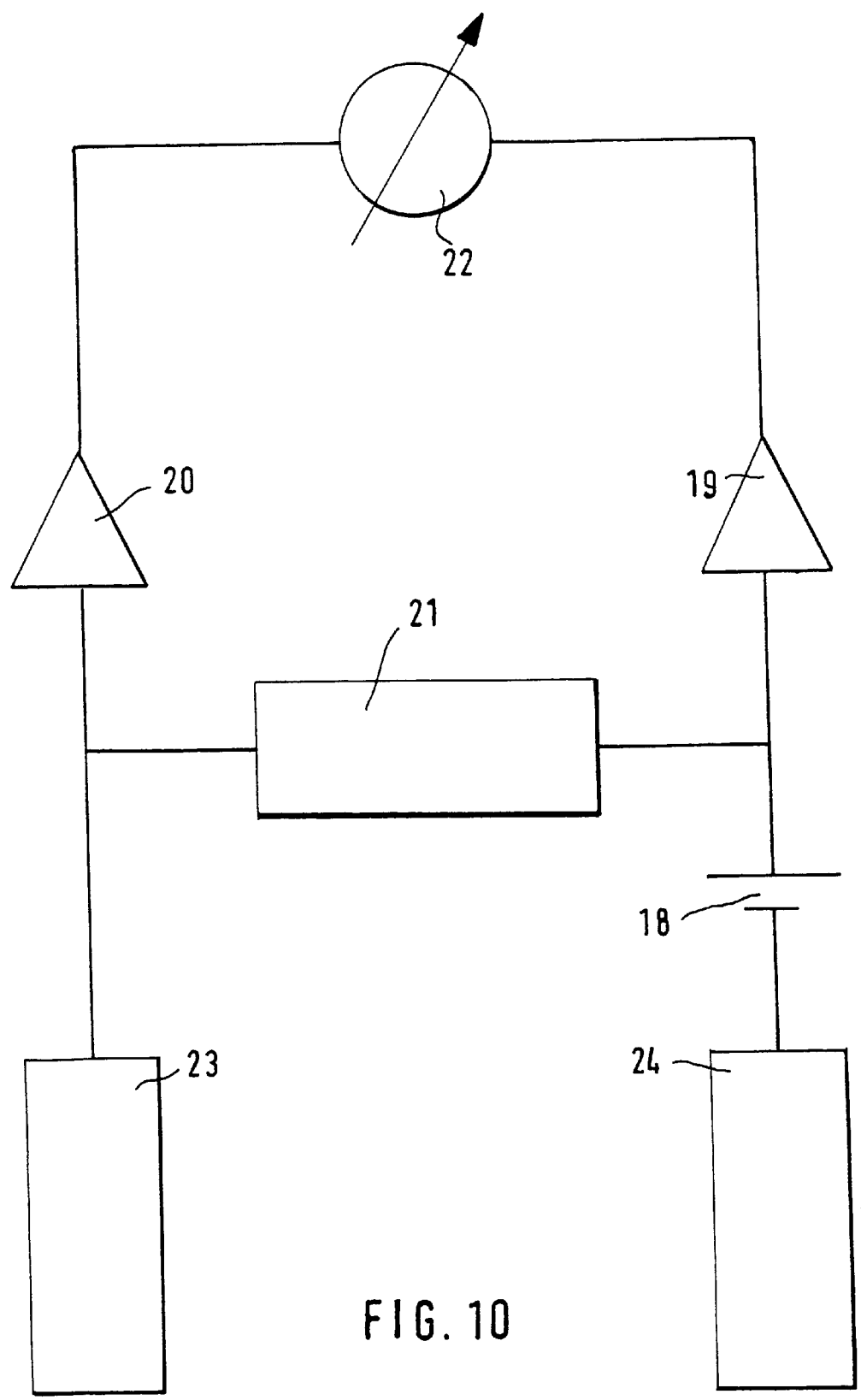
FIG. 10 shows a simplified diagrammatic view of an electronic measuring circuit arrangement for operation of the membrane electrode according to the invention.

FIG. 10 shows in simplified form the diagrammatic structure of an embodimdent of the electronic measuring circuit arrangement used, without however showing the element or elements for processing and storage of the measurement values. The circuit shown in simplified form comprises a stabilised polarisation voltage source 18, two high-impedance amplifiers 19 and 20, a parallel resistor 21 and a display means 22 which in the simplest case can be formed by a voltmeter, as well as the membrane electrode according to the invention as indicated at 23 and a reference electrode 24.

Figure 11:
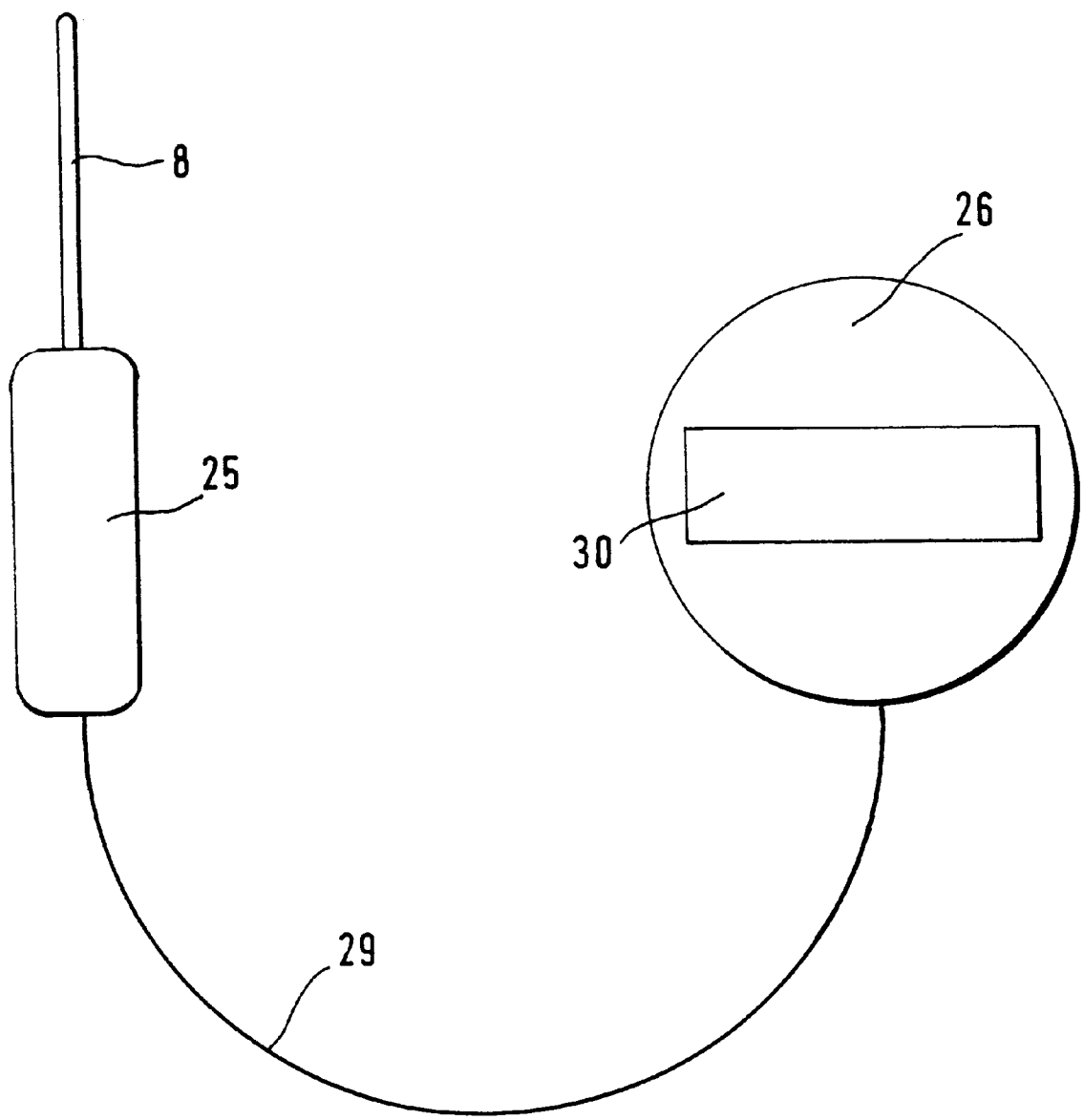
FIGS. 11 and 12 are diagrammatic views of two embodiments of the electronic measuring circuit arrangement shown in FIG. 10.
Figure 12:
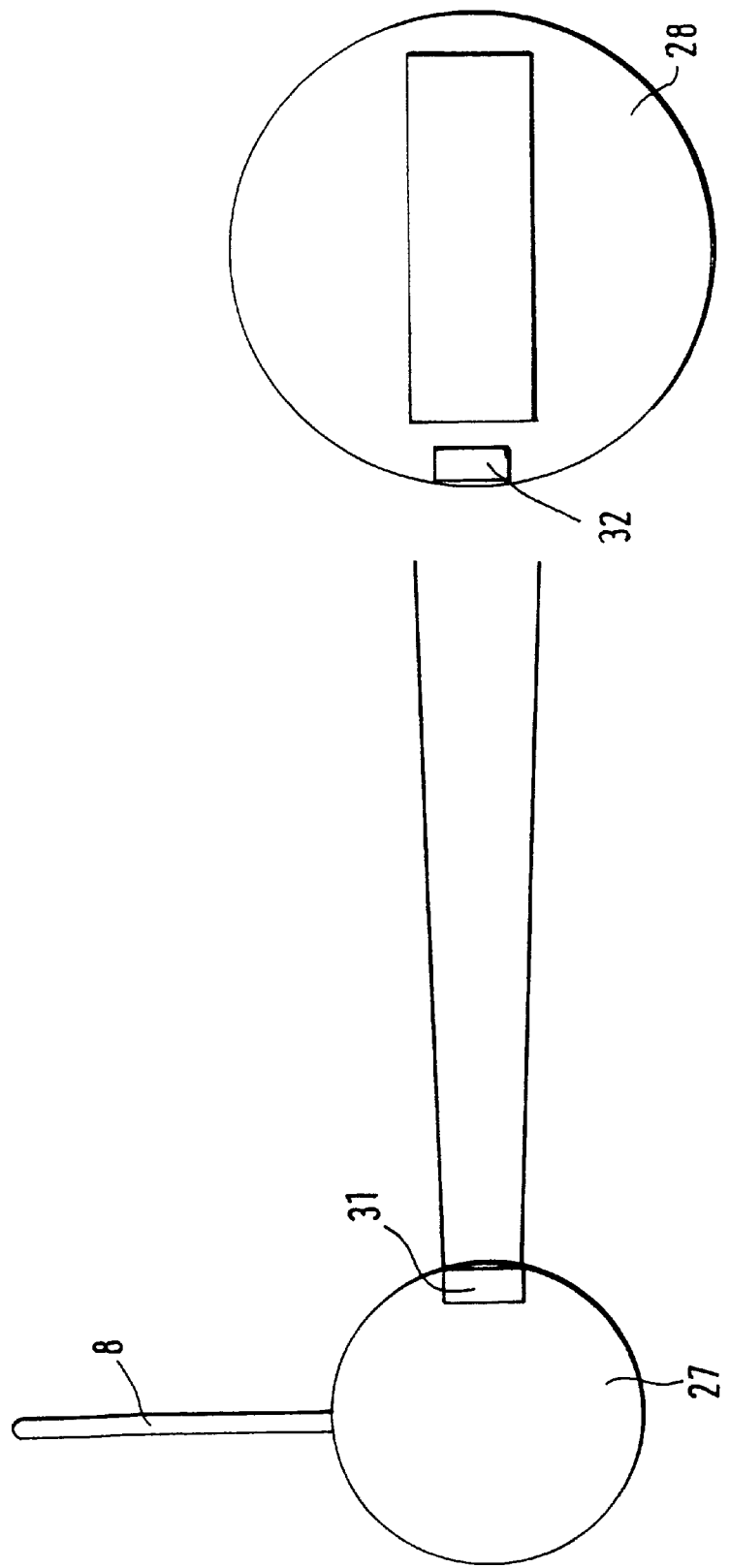

FIGS. 11 and 12 diagrammatically show two advantageous embodiments of the electronic measuring arrangement, in which the electronic measuring arrangement is divided into two units 25, 26, and 27, 28 respectively, which are spatially separated from each other. In the case of the embodiment illustrated in FIG. 11 the unit 25 is connected to the membrane electrode by way of the cable 8 and to the unit 26 by the cable 29. In this embodiment, integrated in the unit 25, being the amplifier unit, is an impedance converter, a differential amplifier, the battery and the voltage stabiliser, the parallel resistor, the reference electrode or reference system, and a current/voltage converter, while integrated in the unit 26, a microprocessor with memory, are a numerical display 30, alternatively to integration in the unit 25 the battery and the voltage stabiliser and an output to a modem or a printer.

The embodiment shown in FIG. 12 provides that the unit 27 is connected to the unit 28 by electro-optical means. The unit 27 therefore contains the components of the unit 25 and an IR-laser diode or an LED while the unit 28 contains the components of the unit 26 and a photoelectric diode 30.

Figure 13:
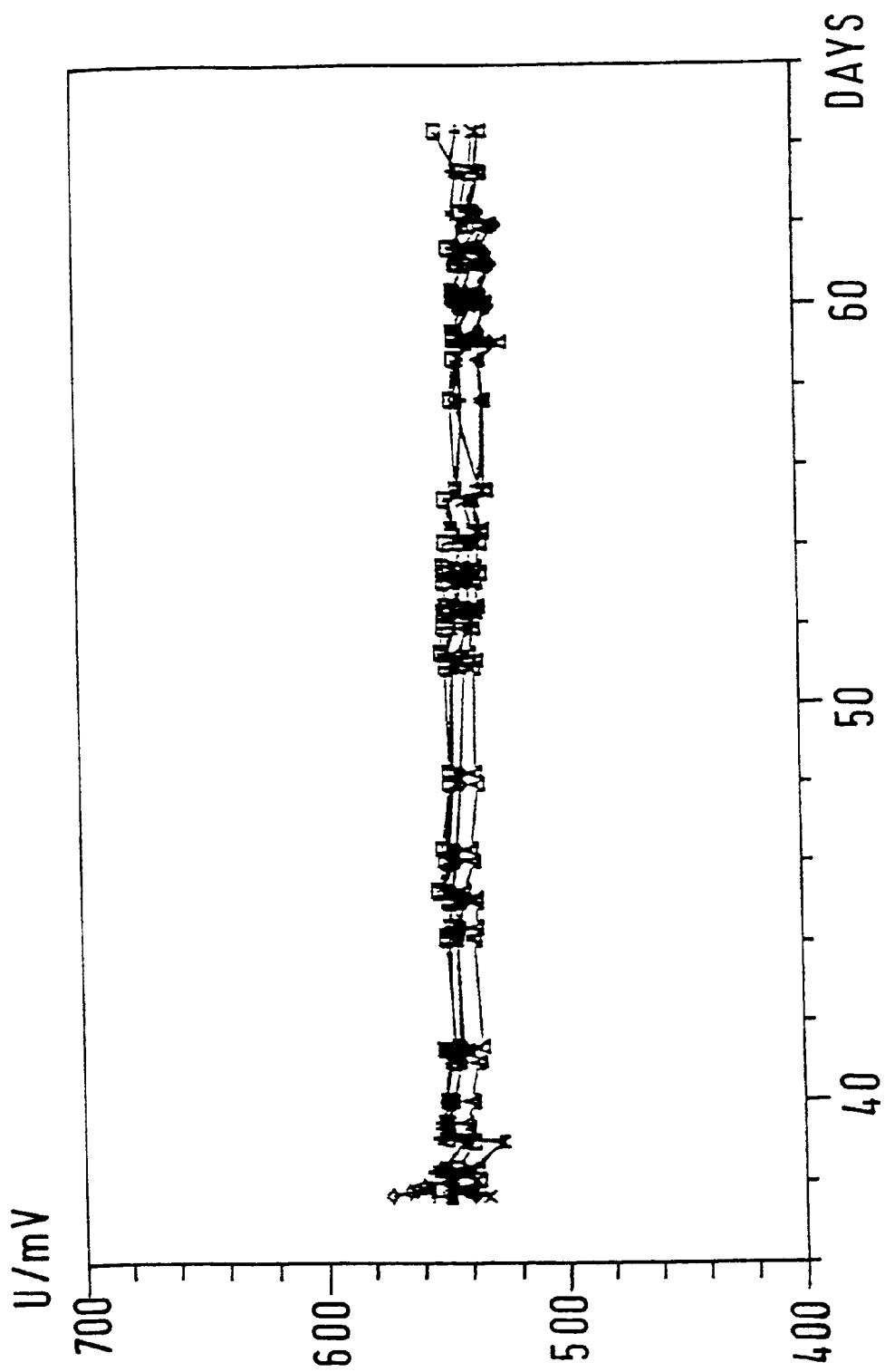
FIG. 13 is a plotting of measurement values obtained in a long-term measurement procedure with five membrane electrodes according to the invention.

FIG. 13 shows the result of long-term measurements over 60 days with five different electrodes. The solutions investigated in these measurement procedures contained 1 mMol $H_2O_2$/l and a parallel resistor having a resistance of $10^9 \Omega$ was used. Taking the recorded measurement results as the basis, the drift of the electrodes was calculated at only 0.003 mV/h or 7.2 m/V in 100 days, whereby the particular suitability of the electrodes according to the invention for long-term measurements is thus made clear.

It will be appreciated that the above-described embodiments of the invention have been set forth only by way of example and illustration thereof and that various other modifications and alterations may be made therein without thereby departing from the spirit and scope of the invention.

What is claimed is:

1. A membrane electrode for measuring the level of glucose concentration in a liquid, comprising:

a base membrane having a first side, at least one noble metal electrode on said first side of the base membrane, a proton-selective ion membrane on the base membrane and the noble metal electrode, and a double membrane which is arranged on the ion membrane and in which glucose oxidase is contained in a suitable medium.

2. A membrane electrode as set forth in claim 1, wherein the base membrane is arranged on an insulating membrane.

3. A membrane electrode as set forth in claim 2, further comprising:

an outer membrane enclosing the insulating membrane, the base membrane with the electrode and the proton-selective ion membrane, wherein the double membrane is arranged on the outer membrane.

4. A membrane electrode as set forth in claim 3, including:

an intermediate space between the insulating membrane, the base membrane with the electrode, the proton-selective ion membrane and the outer membrane; and an electrolyte gel filling said intermediate space.

5. A membrane electrode as set forth in claim 1, wherein the base membrane is arranged on a carrier foil.

6. A membrane electrode as set forth in claim 5, further comprising:

an outer membrane enclosing a carrier foil, the base membrane with the electrode and the proton-selective ion membrane, wherein the double membrane is arranged on the outer membrane.

7. A membrane electrode as set forth in claim 6, including:

an intermediate space between the carrier foil, the base membrane with the electrode, the proton-selective ion membrane and the outer membrane; and an electrolyte gel filling said intermediate space.

8. A membrane electrode as set forth in claim 1, wherein an insulating membrane laterally encloses the electrode structure.

9. A membrane electrode as set forth in claim 1, wherein a carrier foil laterally encloses the electrode structure.

10. A membrane electrode as set forth in claim 1, further comprising:

an outer membrane enclosing the base membrane with the electrode and the proton-selective ion membrane, wherein the double membrane is arranged on the outer membrane.

11. A membrane electrode as set forth in claim 10, further comprising:

an outer membrane enclosing the base membrane with the noble metal electrode and the proton-selective ion membrane;

a cable for connection of said noble metal electrode to an electronic measuring arrangement; and a hose extending from the electrode membrane structure and accommodating the cable, the hose being attached to the outer membrane.

12. A membrane electrode as set forth in claim 11, including:

an intermediate space between the cable and the hose filled with an electrolyte gel.

13. A membrane electrode as set forth in claim 11, wherein the hose is welded to the outer membrane.

14. A membrane electrode as set forth in claim 11, wherein the hose is glued to the outer membrane.

15. A membrane electrode as set forth in claim 1, further comprising:

a cable for connection of said noble metal electrode to an electronic measuring arrangement; and a hose extending from the electrode membrane structure and accommodating the cable.

16. A membrane electrode as set forth in claim 15, including:

an intermediate space between the cable and the hose filled with an electrolyte gel.

17. A membrane electrode as set forth in claim 1, wherein the electrode comprises gold.

18. A membrane electrode as set forth in claim 1, wherein the electrode comprises platinum.

19. A membrane electrode as set forth in claim 1, wherein the ion membrane contains a liquid phase, and wherein ligand molecules are contained in the liquid phase.

20. A membrane electrode as set forth in claim 19, wherein the ligand molecules are tridodecylamine.

21. A membrane electrode as set forth in claim 11, further comprising:

a thermal sensor in the electrode structure.

22. A membrane electrode as set forth in claim 1, wherein the electrode structure has a plurality of measuring locations.

23. A membrane electrode as set forth in claim 22, wherein the measuring locations comprise noble metal electrodes.

24. A membrane electrode as set forth in claim 1, including:

a holding means on which the electrode structure is arranged.

25. A membrane electrode as set forth in claim 24, wherein the holding means is adapted to be fitted on to at least one tooth.

26. A membrane electrode as set forth in claim 24, wherein the holding means is formed by a clamp.

27. A membrane electrode as set forth in claim 1, further comprising:

a pad in which the electrode structure is arranged, direct contact of the glucose oxidase-containing double membrane with the surrounding medium being ensured.

28. A membrane electrode as set forth in claim 27, wherein the pad is of silicone rubber.

29. A membrane electrode as set forth in claim 1, wherein the electrode arrangement is provided in a capillary.

30. A membrane electrode as set forth in claim 1, wherein the electrode arrangement is coupled to a capillary.

31. A membrane electrode as set forth in claim 1, wherein the base membrane is formed by a plastic fiber, and the electrode, the proton-selective ion membrane and the glucose oxidase-containing double membrane enclose the plastic fiber.

* * * * *

UNITED STATES PATENT AND TRADEMARK OFFICE
CERTIFICATE OF CORRECTION

PATENT NO. : 6,176,988 B1
DATED : January 23, 2001
INVENTOR(S) : Manfred Kessler It is certified that error appears in the above-identified patent and that said Letters Patent is hereby corrected as shown below:

Column 6,
Line 66, the patent now reads "in which 31 is contained"; this should read -- in which glucose oxidase 31 is contained --.

Title page,
Illustrative figure and Figure 1, glucose oxidase, represented by reference numeral 31, should be shown as follows:

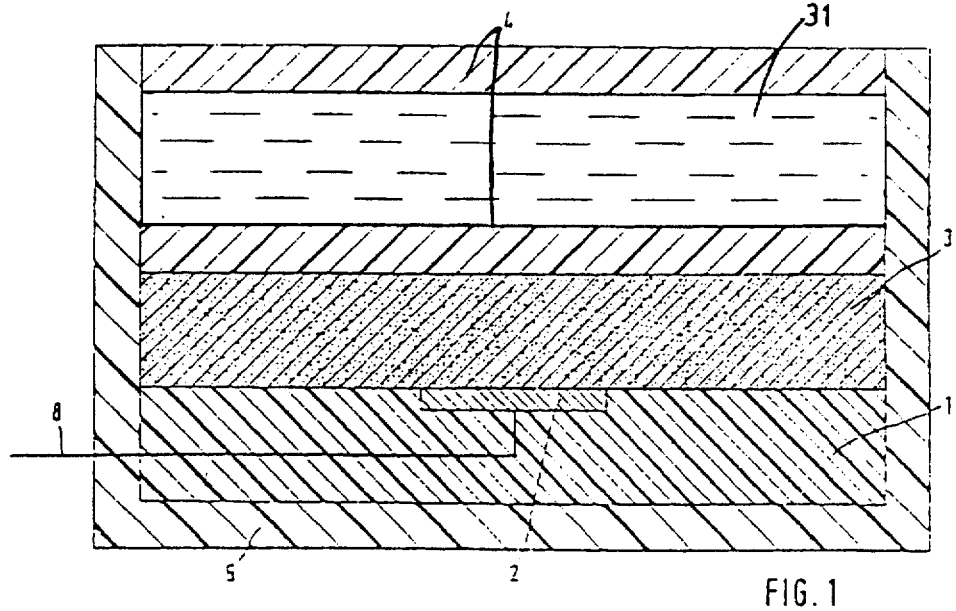

FIG. 1

UNITED STATES PATENT AND TRADEMARK OFFICE
CERTIFICATE OF CORRECTION

PATENT NO. : 6,176,988 B1
DATED : January 23, 2001
INVENTOR(S) : Manfred Kessler It is certified that error appears in the above-identified patent and that said Letters Patent is hereby corrected as shown below:

Figure 2,
Glucose oxidase, represented by reference numeral 31, should be shown as follows:

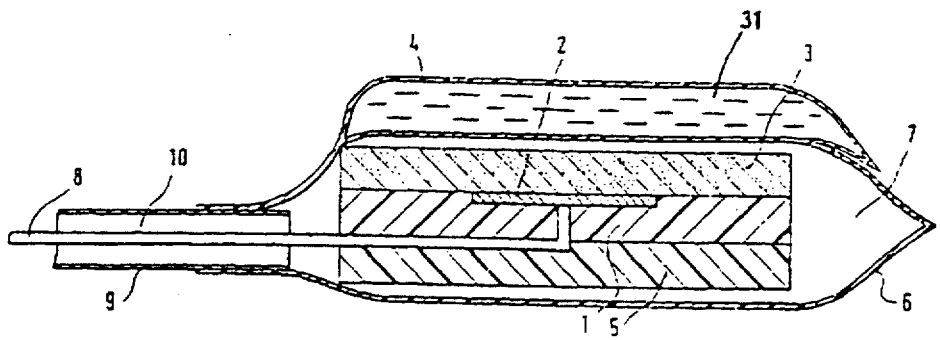

FIG. 2

UNITED STATES PATENT AND TRADEMARK OFFICE
CERTIFICATE OF CORRECTION

PATENT NO.      : 6,176,988 B1
DATED           : January 23, 2001
INVENTOR(S)     : Manfred Kessler It is certified that error appears in the above-identified patent and that said Letters Patent is hereby corrected as shown below:

Figure 3,
Glucose oxidase, represented by reference numeral 31, should be shown as follows:

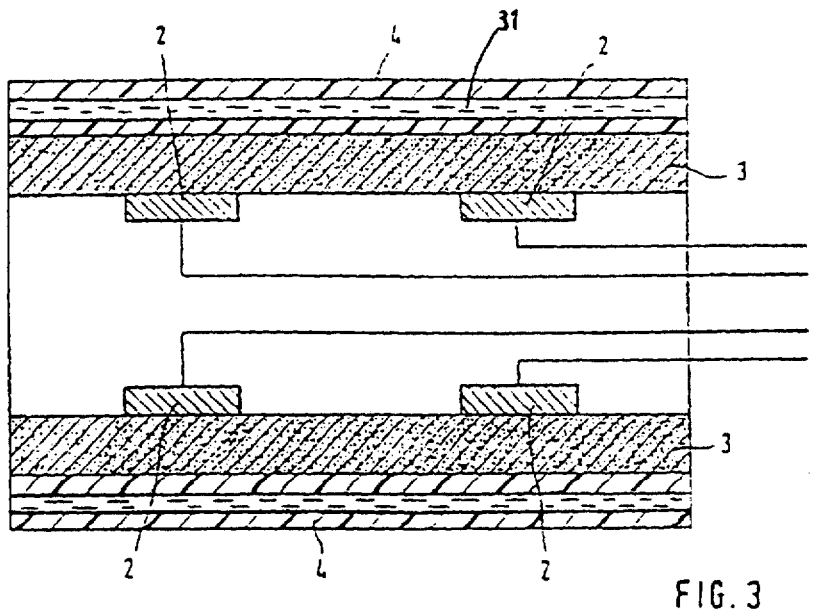

FIG. 3

UNITED STATES PATENT AND TRADEMARK OFFICE
CERTIFICATE OF CORRECTION

PATENT NO.    : 6,176,988 B1                                          Page 4 of 5
DATED         : January 23, 2001
INVENTOR(S)   : Manfred Kessler It is certified that error appears in the above-identified patent and that said Letters Patent is hereby corrected as shown below:

Figure 7,
Glucose oxidase, represented by reference numeral 31, should be shown as follows:

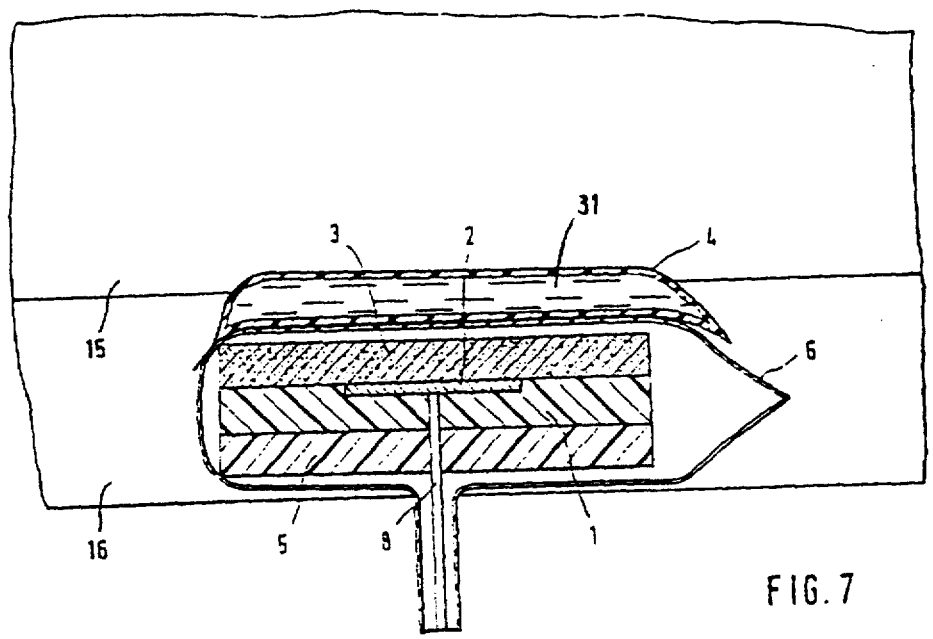

UNITED STATES PATENT AND TRADEMARK OFFICE
CERTIFICATE OF CORRECTION

PATENT NO. : 6,176,988 B1
DATED : January 23, 2001
INVENTOR(S) : Manfred Kessler Page 5 of 5

It is certified that error appears in the above-identified patent and that said Letters Patent is hereby corrected as shown below:

<u>Figure 9</u>,
Glucose oxidase, represented by reference numeral 31, should be shown as follows:

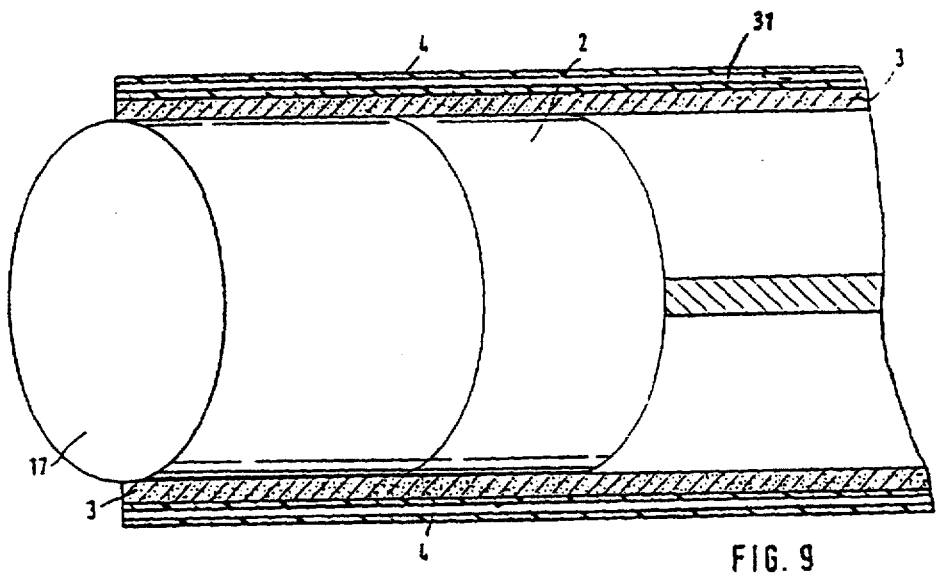

FIG. 9

Signed and Sealed this

Eighth Day of January, 2002

Attest:

JAMES E. ROGAN
*Attesting Officer*   *Director of the United States Patent and Trademark Office*